US012790266B2

(12) United States Patent
Finke et al.

(10) Patent No.: US 12,790,266 B2
(45) Date of Patent: *Nov. 10, 2026

(54) PROCESS TO MAKE CALCIUM OXIDE OR ORDINARY PORTLAND CEMENT FROM CALCIUM BEARING ROCKS AND MINERALS

(71) Applicants: California Institute of Technology, Pasadena, CA (US); Brimstone Energy Inc., Oakland, CA (US)

(72) Inventors: Cody E. Finke, Pasadena, CA (US); Hugo F. Leandri, Pasadena, CA (US)

(73) Assignees: California Institute of Technology, Pasadena, CA (US); Brimstone Energy Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,534

(22) Filed: Jun. 14, 2023

(65) Prior Publication Data

US 2023/0339807 A1 Oct. 26, 2023

Related U.S. Application Data

(63) Continuation of application No. 17/894,621, filed on Aug. 24, 2022, now Pat. No. 11,718,558, which is a (Continued)

(51) Int. Cl.

*C04B 2/10* (2006.01)
*C01F 7/56* (2022.01)

(Continued)

(52) U.S. Cl.

CPC .................. *C04B 2/10* (2013.01); *C01F 7/56* (2013.01); *C04B 11/005* (2013.01); *C04B 11/30* (2013.01);

(Continued)

(58) Field of Classification Search

USPC .......................................................... 423/529

See application file for complete search history.

(56) References Cited

U.S. PATENT DOCUMENTS

| | | | |
|---|---|---|---|
| 2,863,726 | A | 12/1958 | Jonas |
| 4,069,063 | A | 1/1978 | Ball |

(Continued)

FOREIGN PATENT DOCUMENTS

| | | |
|---|---|---|
| CA | 1327694 | 3/1994 |
| CA | 2240067 | 6/1997 |

(Continued)

OTHER PUBLICATIONS

Dergacheva et al. (2009) “Basalt Leaching with Orthophosphoric Acid,” Inorganic Materials (45)12: 1366-1369.

(Continued)

*Primary Examiner* — Coris Fung
*Assistant Examiner* — Catriona M Corallo
(74) *Attorney, Agent, or Firm* — Leydig, Voit & Mayer, Ltd.

(57) ABSTRACT

Aspects of the invention include a method of producing a cement material comprising step of: first reacting a calcium-bearing starting material with a first acid to produce an aqueous first calcium salt; second reacting the aqueous first calcium salt with a second acid to produce a solid second calcium salt; wherein the second acid is different from the first acid and the second calcium salt is different from the first calcium salt; and thermally treating the second calcium salt to produce a first cement material. Preferably, but not necessarily, during the second reacting step, reaction between the first calcium salt and the second acid regenerates the first acid.

30 Claims, 3 Drawing Sheets

Related U.S. Application Data continuation of application No. 16/992,318, filed on Aug. 13, 2020.

(60) Provisional application No. 63/019,916, filed on May 4, 2020, provisional application No. 62/932,200, filed on Nov. 7, 2019, provisional application No. 62/913,620, filed on Oct. 10, 2019, provisional application No. 62/886,137, filed on Aug. 13, 2019.

(51) Int. Cl.

| | |
|---|---|
| ***C04B 11/00*** | (2006.01) |
| ***C04B 11/30*** | (2006.01) |
| ***C04B 22/06*** | (2006.01) |
| ***C04B 28/04*** | (2006.01) |
| ***C04B 40/00*** | (2006.01) |
| *C01G 49/14* | (2006.01) |
| *C07C 1/32* | (2006.01) |

(52) U.S. Cl.
CPC ............ *C04B 22/064* (2013.01); *C04B 28/04* (2013.01); *C04B 40/0046* (2013.01); *C01G 49/14* (2013.01); *C07C 1/328* (2013.01)

(56) References Cited

U.S. PATENT DOCUMENTS

| | | | |
|---|---|---|---|
| 4,158,042 | A | 6/1979 | Deutschman |
| 4,487,784 | A | 12/1984 | Kuroda et al. |
| 4,966,757 | A | 10/1990 | Lewis et al. |
| 5,049,198 | A | 9/1991 | Ribas |
| 5,211,745 | A | 5/1993 | Motteram et al. |
| 6,051,196 | A | 4/2000 | Singh et al. |
| 6,171,564 | B1 | 1/2001 | Jones |
| 6,471,743 | B1 | 10/2002 | Young et al. |
| 6,494,932 | B1 | 12/2002 | Abercrombie |
| 6,500,396 | B1 | 12/2002 | Lakshmanan et al. |
| 6,551,378 | B2 | 4/2003 | Farone et al. |
| 6,562,308 | B1 | 5/2003 | Carstens et al. |
| 6,613,141 | B2 | 9/2003 | Key, Jr. |
| 6,835,244 | B2 | 12/2004 | Oates et al. |
| 6,866,702 | B2 | 3/2005 | Mitsuda |
| 6,984,328 | B2 | 1/2006 | Sasowsky et al. |
| 7,261,874 | B2 | 8/2007 | Lahoda et al. |
| 7,329,396 | B2 | 2/2008 | Harris et al. |
| 7,335,342 | B2 | 2/2008 | Jasra et al. |
| 7,422,621 | B2 | 9/2008 | Ando et al. |
| 7,604,783 | B2 | 10/2009 | King et al. |
| 7,666,372 | B2 | 2/2010 | Puvvada et al. |
| 7,682,589 | B2 | 3/2010 | Gorset et al. |
| 7,749,476 | B2 | 7/2010 | Constantz et al. |
| 7,763,221 | B2 | 7/2010 | Wallevik et al. |
| 7,794,685 | B2 | 9/2010 | Rauser et al. |
| 7,803,336 | B2 | 9/2010 | Lakshmanan et al. |
| 7,837,961 | B2 | 11/2010 | Boudreault et al. |
| 7,896,949 | B2 | 3/2011 | Ku et al. |
| 7,947,239 | B2 | 5/2011 | Lackner et al. |
| 7,964,015 | B2 | 6/2011 | Creasey et al. |
| 8,043,594 | B2 | 10/2011 | Lackner et al. |
| 8,043,597 | B2 | 10/2011 | Daum et al. |
| 8,066,813 | B2 | 11/2011 | Pratt |
| 8,110,166 | B2 | 2/2012 | Gunnarsson |
| 8,114,371 | B2 | 2/2012 | Gunnarsson et al. |
| 8,206,655 | B2 | 6/2012 | Gong et al. |
| 8,241,594 | B2 | 8/2012 | Boudreault et al. |
| 8,337,789 | B2 | 12/2012 | Boudreault et al. |
| 8,337,795 | B2 | 12/2012 | Barati et al. |
| 8,413,420 | B1 | 4/2013 | Zaromb |
| 8,597,600 | B2 | 12/2013 | Boudreault et al. |
| 8,673,257 | B2 | 3/2014 | Reddy et al. |
| 8,795,508 | B2 | 8/2014 | Jones |
| 8,857,118 | B2 | 10/2014 | Constantz et al. |
| 8,894,740 | B2 | 11/2014 | Harris et al. |
| 8,900,545 | B2 | 12/2014 | Martinez Martinez et al. |
| 8,956,526 | B2 | 2/2015 | Gorensek |
| 8,974,757 | B2 | 3/2015 | Park et al. |
| 9,023,301 | B2 | 5/2015 | Boudreault et al. |
| 9,034,101 | B2 | 5/2015 | Ronin |
| 9,057,136 | B2 | 6/2015 | Weidner et al. |
| 9,108,151 | B2 | 8/2015 | Brent |
| 9,115,419 | B2 | 8/2015 | Lakshmanan et al. |
| 9,126,865 | B2 | 9/2015 | Blackstock et al. |
| 9,138,681 | B2 | 9/2015 | Elmaleh |
| 9,181,603 | B2 | 11/2015 | Boudreault et al. |
| 9,194,021 | B2 | 11/2015 | Walder |
| 9,212,092 | B2 | 12/2015 | Herfort et al. |
| 9,228,248 | B2 | 1/2016 | Sugita et al. |
| 9,260,767 | B2 | 2/2016 | Boudreault et al. |
| 9,290,828 | B2 | 3/2016 | Boudreault et al. |
| 9,339,761 | B2 | 5/2016 | Jones et al. |
| 9,353,425 | B2 | 5/2016 | Boudreault et al. |
| 9,359,221 | B2 | 6/2016 | Jones et al. |
| 9,382,600 | B2 | 7/2016 | Boudreault et al. |
| 9,440,189 | B2 | 9/2016 | Mercier et al. |
| 9,469,546 | B2 | 10/2016 | Gartner et al. |
| 9,527,775 | B2 | 12/2016 | Sorrell et al. |
| 9,534,274 | B2 | 1/2017 | Boudreault et al. |
| 9,556,500 | B2 | 1/2017 | Boudreault et al. |
| 9,631,257 | B2 | 4/2017 | Pisch et al. |
| 9,724,671 | B2 | 8/2017 | Belchior et al. |
| 9,862,641 | B2 | 1/2018 | Anast et al. |
| 9,889,421 | B2 | 2/2018 | Harris et al. |
| 9,890,441 | B2 | 2/2018 | Pingitore, Jr. |
| 9,896,741 | B2 | 2/2018 | Bu et al. |
| 9,963,351 | B2 | 5/2018 | Priestnall |
| 9,963,352 | B2 | 5/2018 | Aranda et al. |
| 10,000,646 | B2 | 6/2018 | Chen et al. |
| 10,006,102 | B2 | 6/2018 | Xiong et al. |
| 10,112,842 | B2 | 10/2018 | Fournier et al. |
| 10,113,407 | B2 | 10/2018 | Rau |
| 10,174,402 | B2 | 1/2019 | Boudreault et al. |
| 10,472,282 | B2 | 11/2019 | Autef |
| 10,537,851 | B2 | 1/2020 | Cardiff |
| 10,563,314 | B2 | 2/2020 | Fournier et al. |
| 10,583,394 | B2 | 3/2020 | Jones et al. |
| 10,662,116 | B2 | 5/2020 | Atakan et al. |
| 10,738,370 | B2 | 8/2020 | Mokmeli et al. |
| 10,745,321 | B2 | 8/2020 | Ciuperca |
| 10,752,508 | B2 | 8/2020 | Fournier et al. |
| 10,787,820 | B1 | 9/2020 | Lee |
| 10,882,786 | B2 | 1/2021 | Camali et al. |
| 10,894,997 | B2 | 1/2021 | Johnson et al. |
| 11,180,860 | B2 | 11/2021 | Finke |
| 2006/0013761 | A1 | 1/2006 | Lahoda et al. |
| 2006/0024224 | A1 | 2/2006 | Neudorf et al. |
| 2009/0000956 | A1 | 1/2009 | Weidner et al. |
| 2009/0301352 | A1 | 12/2009 | Constantz et al. |
| 2010/0313794 | A1 | 12/2010 | Constantz et al. |
| 2011/0217220 | A1 | 9/2011 | McLellan et al. |
| 2011/0290153 | A1 | 12/2011 | Abdullah et al. |
| 2012/0034154 | A1 | 2/2012 | McHugh et al. |
| 2012/0067740 | A1 | 3/2012 | Gasik et al. |
| 2012/0204680 | A1 | 8/2012 | Duyvesteyn |
| 2012/0291675 | A1 | 11/2012 | Camire et al. |
| 2016/0177417 | A1 | 6/2016 | Ospanov et al. |
| 2017/0320781 | A1 | 11/2017 | Atakan et al. |
| 2020/0224290 | A1 | 7/2020 | Oraby et al. |
| 2020/0316524 | A1 | 10/2020 | Jones et al. |
| 2021/0070656 | A1 | 3/2021 | Finke et al. |
| 2022/0064063 | A1 | 3/2022 | Chiang et al. |
| 2022/0106691 | A1 | 4/2022 | Finke |
| 2022/0145477 | A1 | 5/2022 | Chiang et al. |
| 2022/0411940 | A1 | 12/2022 | Finke |

FOREIGN PATENT DOCUMENTS

| | | | |
|---|---|---|---|
| CA | 2340567 | A1 | 9/2002 |
| CA | 2513309 | C | 6/2010 |
| CA | 2613698 | C | 2/2013 |
| CA | 2812309 | C | 12/2014 |
| CA | 2885255 | C | 12/2015 |
| CA | 2962070 | A1 | 4/2016 |
| CA | 2789095 | C | 3/2018 |

(56) References Cited

FOREIGN PATENT DOCUMENTS

| | | | |
|---|---|---|---|
| CA | 2788384 | C | 2/2019 |
| CA | 2882181 | C | 5/2019 |
| CA | 3038320 | C | 8/2021 |
| CN | 101671848 | | 3/2010 |
| CN | 101668550 | B | 2/2014 |
| CN | 106468056 | | 3/2017 |
| CN | 106468056 | A | 3/2017 |
| EP | 0004568 | | 10/1979 |
| EP | 0039745 | A1 | 11/1981 |
| EP | 862659 | B1 | 8/2000 |
| EP | 1258535 | B1 | 8/2003 |
| EP | 1228259 | B1 | 12/2003 |
| EP | 1487753 | B1 | 11/2005 |
| EP | 1412544 | B1 | 1/2006 |
| EP | 1809778 | B1 | 7/2009 |
| EP | 1572588 | B1 | 1/2011 |
| EP | 2303429 | A2 | 4/2011 |
| EP | 2468388 | | 6/2012 |
| EP | 1558543 | B1 | 7/2013 |
| EP | 2195469 | B1 | 6/2014 |
| EP | 2679638 | B1 | 9/2015 |
| EP | 2796574 | B1 | 3/2017 |
| EP | 3157883 | B1 | 7/2018 |
| EP | 2999803 | B1 | 10/2018 |
| EP | 2526213 | B1 | 11/2018 |
| EP | 2651846 | B1 | 11/2019 |
| EP | 2337769 | B1 | 12/2019 |
| EP | 3581257 | A1 | 12/2019 |
| EP | 3180290 | B1 | 4/2020 |
| EP | 3224219 | B1 | 6/2020 |
| EP | 3129125 | B1 | 7/2020 |
| EP | 2946024 | B1 | 11/2020 |
| EP | 3262008 | B1 | 12/2020 |
| FI | 121271 | | 9/2010 |
| JP | 2001017939 | A | 1/2001 |
| JP | 2005-145785 | | 6/2005 |
| JP | 2008-246398 | A | 10/2008 |
| JP | 2008-246445 | A | 10/2008 |
| JP | 2011-527664 | A | 1/2010 |
| JP | 2010-527898 | T | 8/2010 |
| JP | 2011-072917 | A | 4/2011 |
| JP | 2012-188338 | A | 10/2012 |
| KR | 10-2014- 0000736 | | 1/2014 |
| RU | 2181391 | C1 | 4/2002 |
| RU | 2440178 | C2 | 1/2012 |
| WO | WO 2005/098062 | A1 | 10/2005 |
| WO | WO 2009/100937 | A2 | 8/2009 |
| WO | WO 2010/006242 | A1 | 1/2010 |
| WO | WO 2011/003918 | A1 | 1/2011 |
| WO | WO 2012/149631 | A1 | 11/2012 |
| WO | WO 2017/077180 | | 5/2017 |
| WO | WO 2018/218294 | A1 | 12/2018 |
| WO | WO 2021/056110 | A1 | 4/2021 |
| WO | WO 2021/222585 | A2 | 11/2021 |
| WO | WO 2022/020572 | A1 | 1/2022 |
| WO | WO 2022/020470 | A8 | 4/2022 |

OTHER PUBLICATIONS

Druecker et al. (2015) "Amended Preliminary Economic Assessment (PEA) for Specialty Alumina Production From the White Mountain Anorthosite Deposit, West Greenland," Hudson Resources Inc., 162 pages.

Ellis et al. (publicly available Sep. 2019) "Toward electrochemical synthesis of cement—An electrolyzer-based process for decarbonating $CaCO_3$ while producing useful gas streams," PNAS (Jun. 2020) 117(23): 12584-12591.

Extended European Search Report dated Feb. 7, 2022 in European Application No. 19804349.9, 8 pp.

Garrick et al. (Dec. 2017) "Characterizing Voltage Losses in an $SO_2$ Depolarized Electrolyzer Using Sulfonated Polybenzimidazole Membranes," ECS 164(14): F1591-F1595.

Golden et al. (2005) "Laboratory-simulated acid-sulfate weathering of basaltic materials: Implications for formation of sulfates at Meridiani Planum and Gusev crater, Mars," JGR Planets 110, E12S07: 1-15.

Gong (2015) "Emulating Volcanism to Create a New Class of Recycled Water," Harmon Systems International, LLC & Earth Renaissance Technologies, LLC: 1 page (poster).

Gorensek (2011) "Hybrid sulfur cycle flowsheets for hydrogen production using high-temperature gas-cooled reactors," International Journal of Hydrogen Energy 36: 12725-12741.

Gou et al. (Jan. 2019) "Utilization of tailings in cement and concrete: A review," Sci Eng Compos Mater 26: 449-464.

Hausrath et al. (2013) "Acid sulfate alteration of fluorapatite, basaltic glass and olivine by hydrothermal vapors and fluids: Implications for fumarolic activity and secondary phosphate phases in sulfate-rich Paso Robles soil at Gusev Crater, Mars," JGR Planets 118(1): 1-13.

Horneck et al. (2007) "Acidifying Soil for Crop Production: Inland Pacific Northwest," A Pacific Northwest Extension publication: 1-15.

Lokkiluoto et al. (2010) "Study of SO2-Depolarized Water Electrolysis," 18th World Hydrogen Energy Conference: 105-111.

Lokkiluoto et al. (2012) "Novel process concept for the production of H2 and H2SO4 by SO2-depolarized electrolysis," Environ Dev Sustain 14: 529-540.

Lokkiluoto (2013) "Fundamentals of SO2 depolarized water electrolysis and challenges of materials used," Doctoral Dissertation, Aalto University: 144 pages.

Lu et al. (1981) "Recent developments in the technology of sulphur dioxide depolarized electrolysis," Journal of Applied Electrochemistry 11(3): 347-355.

mining.com Staff Writer (Feb. 2019) "Mine tailings could be used to produce cement replacement material," available online at https://www.mining.com/mine-tailings-used-produce-cement-replacement-material/, 2 pages.

NEMO Project Abstract "Near-zero-waste recycling of low-grade sulphidic mining waste for critical-metal, mineral and construction raw-material production in a circular economy" and "General Presentation" (Apr. 2020): 34 pages.

Padeste et al. (1990) "The influence of transition metals on the thermal decomposition of calcium carbonate in hydrogen," Materials Research Bulletin 25(10): 1299-1305.

Peretyazhko et al. (Mar. 2017) "Smectite Formation in Acid Sulfate Environments on Mars," Lunar and Planetary Science Conference, The Woodlands, TX, 2 pages.

Peretyazhko et al. (publicly available Oct. 2017) "Smectite formation in the presence of sulfuric acid: Implications for acidic smectite formation on early Mars," Geochimica et Cosmochimica Acta (Jan. 2018) 220: 248-260.

Popczun et al. (2014) "Highly Active Electrocatalysis of the Hydrogen Evolution Reaction by Cobalt Phosphide Nanoparticles," Angewandte Chemie 53: 5427-5430.

Popczun et al. (2013) "Nanostructured Nickel Phosphide as an Electrocatalyst for the Hydrogen Evolution Reaction," J. Am. Chem. Soc. 135(25): 9267-9270.

Ryan et al. (1975) "Effect of Surface-applied Sulfuric Acid on Growth and Nutrient Availability of Five Range Grasses in Calcareous Soils," Journal of Range Management 28(5): 411-414.

Search Report and Written Opinion, dated Sep. 6, 2019, corresponding to International Application No. PCT/US2019/032828 (filed May 17, 2019), 16 pp.

Search Report and Written Opinion, dated Nov. 23, 2020, corresponding to International Application No. PCT/US2020/046063 (filed Aug. 13, 2020), 10 pp.

Shaw et al. (2006) "Sulphuric acid decomposition reactions in the sulphur iodine and Westinghouse processes for hydrogen generation," WHEC 16, Lyon France: 1-8.

Simonsen et al. (publicly available Dec. 2019) "Evaluation of mine tailings' potential as supplementary cementitious materials based on chemical, mineralogical and physical characteristics," Waste Management (Feb. 2020) 102: 710-721.

Singh et al. (2002) "Production of Beneficiated Phosphogypsum for Cement Manufacture," Journal of Scientific & Industrial Research 61: 533-537.

(56) References Cited

OTHER PUBLICATIONS

U.S. Office Action dated Oct. 19, 2020, corresponding to U.S. Appl. No. 16/415,275, 10 pages.
U.S. Office Action dated Jan. 29, 2021, corresponding to U.S. Appl. No. 16/415,275, 10 pages.
Weidner (2016) "Electrolyzer performance for producing hydrogen via a solar-driven hybrid-sulfur process," J Appl Electrochem 46:829-839.
Zhang et al. (2000) "Reactions between Hydrogen Sulfide and Sulfuric Acid: A Novel Process for Sulfur Removal and Recovery," Industrial & Engineering Chemistry Research 39(7):2505-2509.
European Search Report issued in European Application Serial No. 20853120.2 dated Aug. 8, 2023.
U.S. Appl. No. 16/415,275, filed May 17, 2019, Patented.
U.S. Appl. No. 17/505,073, filed Oct. 19, 2021, Pending.
U.S. Appl. No. 17/894,674, filed Aug. 24, 2022, Pending.
U.S. Appl. No. 16/992,318, filed Aug. 13, 2020, Pending.
U.S. Appl. No. 17/894,621, filed Aug. 24, 2022, Pending.
Indonesian Office Action issued in Indonesian Application Serial No. P00202201259 dated Sep. 8, 2023.
Search Report corresponding to Russian Patent Application No. 2022103194, completed Apr. 26, 2024.
Official Action corresponding to Russian Patent Application No. 2022103194, issued Apr. 26, 2024.
Official Action corresponding to Brazilian Patent Application No. BR112022002685-4, issued May 20, 2024.
Volzhensky A.V. et al., Mineralnyje Vyazhuschije Materialy (Tekhnologiya I Svojstva), Moscow, Stroyizdat, 1979, 476 pages, pp. 78-98.
Official Action corresponding to Colombian Patent Application No. NC2022/0002780, issued Jul. 16, 2024.
Notice of Reasons for Refusal dated Jun. 3, 2025 corresponding to Japanese Application No. 2022-508875, 7 pages.

PROCESS TO MAKE CALCIUM OXIDE OR ORDINARY PORTLAND CEMENT FROM CALCIUM BEARING ROCKS AND MINERALS

CROSS-REFERENCE TO RELATED APPLICATIONS

This application is a continuation of U.S. patent application Ser. No. 17/894,621, filed Aug. 24, 2022, which is a continuation of U.S. patent application Ser. No. 16/992,318, filed Aug. 13, 2020, which claims the benefit of and priority to U.S. Provisional Application No. 62/886,137, filed Aug. 13, 2019, U.S. Provisional Application No. 62/913,620, filed Oct. 10, 2019, U.S. Provisional Application No. 62/932,200, filed Nov. 7, 2019, and U.S. Provisional Application No. 63/019,916, filed May 4, 2020, each of which is hereby incorporated by reference in its entirety to the extent not inconsistent herewith.

BACKGROUND OF INVENTION

The art of producing cement materials, including Ordinary Portland Cement, faces considerable challenges, inefficiencies, and/or drawbacks. For example, conventional processes for producing cement are energy intensive, produce environment-degrading byproducts such as $CO_2$ and/or $SO_2$, and utilize only a limited range of feedstocks, primarily simple calcium-based materials such as calcium carbonate (limestone) or mined calcium sulfate (gypsum). This application addresses these and other challenges in the art.

SUMMARY OF THE INVENTION

Provided herein are methods for producing cement materials that have any combination of the following advantages or features: less energy intensive than prior approaches, with some embodiments being net energy neutral or even net energy producing, regenerate certain reagents, characterized by a net reaction free of $SO_2$ and/or $CO_2$, recycle certain byproducts, do not include producing $CO_2$, can utilize a wider range of feedstock materials, including more complex materials, generate value-added side products, and/or generate composite cement materials.

Included herein are methods for producing cement materials using a two-acid approach, where materials are reacted with two different acids and/or two different acid reaction steps. Advantages of these approaches include all or a majority of the above mentioned advantages and features. For example, the disclosed two-acid approach provides for the ability to digest complex calcium-bearing materials, including those with Ca as well as other metal (including metalloid) elements such Si, Al, and other species, and even forming value-added side products from those non-Ca metals, while also regenerating reagent acids. Significantly, these methods can also be free of $CO_2$ generation and can include converting $SO_2$ into a reagent acid, thereby eliminating or dramatically reducing $SO_2$ emissions for $CaSO_4$ based approaches to cement manufacturing.

Aspects of the invention include a method of producing a cement material comprising steps of: first reacting a calcium-bearing starting material with a first acid to produce an aqueous first calcium salt; second reacting the aqueous first calcium salt with a second acid to produce a solid second calcium salt; wherein the second acid is different from the first acid and the second calcium salt is different from the first calcium salt; and thermally treating one or more calcium salts to produce a first cement material. Preferably, but not necessarily, the one or more calcium salts is the second calcium salt. Preferably, but not necessarily, during the second reacting step, reaction between the first calcium salt and the second acid regenerates the first acid. Preferably, but not necessarily, the methods are characterized by a net reaction free of an acid-forming gas product. Preferably, but not necessarily, the method comprises forming the solid second calcium salt characterized by a purity of greater than or equal to 90 dry wt. % purity. Preferably, but not necessarily, any of the methods disclosed herein include a first separating step after the first reacting step and before the second reacting step; the first separating step comprising separating a first aqueous fraction from a first solid fraction; wherein the first aqueous fraction comprises the aqueous first calcium salt and the first solid fraction comprises one or more solid byproducts formed during the first reacting step. Preferably, but not necessarily, any of the methods disclosed herein include a second separating step after the second reacting step and before the thermally treating step; the second separating step comprising separating a second solid fraction from a second aqueous fraction; wherein the second solid fraction comprises the solid second calcium salt and the second aqueous fraction comprises one or more aqueous byproducts formed during the second reacting step. Preferably, the solid fraction is characterized by a dry mass at least 90 wt. % of which is the second calcium salt.

Preferably, but not necessarily, any of the methods disclosed herein include a second acid regeneration step; wherein the second acid regeneration step comprises converting one or more gas products of the thermally treating step to the second acid. Optionally, the second acid regeneration step is a non-electrochemical process performed according to formula FX1A: $SO_2+\frac{1}{2}O_2+H_2O \rightarrow H_2SO_4$ (FX1A) wherein: the $SO_2$ in FX1A is a gas product of the thermally treating step; the $H_2SO_4$ generated in FX1A is used as at least a fraction of the second acid during the second reacting step. Optionally, the second acid regeneration step is a non-electrochemical process performed according to formula FX1B: $SO_2+H_2O \rightarrow H_2SO_3$ (FX1B) wherein: the $SO_2$ in FX1B is a gas product of the thermally treating step; the $H_2SO_3$ generated in FX1B is used as at least a fraction of the second acid during the second reacting step. Optionally, the second acid regeneration step comprises (i) electrochemically oxidizing sulfur dioxide to sulfuric acid and (ii) forming hydrogen gas via a reduction reaction; and wherein the second acid regeneration step is performed according to formula FX2: $SO_2+2H_2O \rightarrow H_2SO_4+H_2$ (FX2); wherein: the $SO_2$ in FX2 is a gas product of the thermally treating step; the $H_2SO_4$ generated in FX2 is used as at least a fraction of the second acid during the second reacting step. Optionally, the thermally treating step comprises using energy generated from oxidizing the hydrogen gas formed as a result of the second acid regeneration. For example, the hydrogen gas produced via the method can be used to power the electrochemical step, such as via a fuel cell or turbine. Optionally, the electrochemically oxidizing sulfur dioxide comprises using energy generated as a result of the second acid regeneration step. It is noted that when $H_2SO_4$ is added to a solution that contains both $MgCl_2$ and $CaCl_2$), only $CaSO_4$ will precipitate. If $H_2SO_3$ is added to a solution of $MgCl_2$ and $CaCl_2$), both $MgSO_3$ and $CaSO_3$ will precipitate. Of consideration is that there are currently regulations against having Mg in cement, such that the calcium-bearing starting material preferably has a low-Mg content so minimize amount of Mg material precipitated.

Optionally, during the second reacting step, reaction between the first calcium salt and the second acid regenerates the first acid according to formula FX3: $CaCl_{2(aq)}+H_2SO_4 \rightarrow CaSO_{4(s)}+2HCl$ (FX3); wherein: the first calcium salt is $CaCl_2$); the first acid is HCl; the second acid is $H_2SO_4$; and the second calcium salt is $CaSO_4$.

The calcium-bearing starting material comprises Ca. The calcium-bearing starting material has a chemical composition comprising the element Ca. Preferably, the calcium-bearing starting material has a chemical composition comprising the element Ca wherein the weight percent and/or the molar percent of Ca in said calcium-bearing starting material is at least 0.001%, preferably at least 0.01%, preferably at least 0.1%, more preferably at least 1&, further more preferably at least 5%, still more preferably at least 10%, and yet more preferably at least 20%. Optionally, in any of the methods disclosed herein, the calcium-bearing starting material has a chemical composition comprising the element Ca wherein the weight percent and/or the molar percent of Ca in said calcium-bearing starting material is selected from the range of 1% to 80%, optionally 1% to 60%, optionally 1% to 55%, optionally 1% to 50%. Optionally, in any of the methods disclosed herein, the calcium-bearing starting material comprises at least one multinary metal oxide material having a composition comprising Ca and at least one other metal element selected from the group consisting of Al, Si, Fe, Mn, and Mg. Optionally, the composition of the at least one multinary metal oxide comprises less than or equal to 55 wt. % of Ca. Optionally, the composition of the at least one multinary metal oxide comprises less than or equal to 60 wt. % of Ca. Optionally, in any of the methods disclosed herein, the at least one multinary metal oxide material is at least one natural rock or mineral. Optionally, in any of the methods disclosed herein, the at least one natural rock or mineral comprises basalt, igneous appetites, wollastonite, anorthosite, montmorillonite, bentonite, calcium-containing feldspar, anorthite, diopside, pyroxene, pyroxenite, mafurite, kamafurite, clinopyroxene, colemonite, grossular, augite, pigeonite, margarite, calcium serpentine, garnet, scheilite, skarn, limestone, natural gypsum, appetite, fluorapatite, or any combination of these. Optionally, in any of the methods disclosed herein, calcium-bearing starting material comprises cement, concrete, Portland cement, fly ash, slag, or any combination of these. If the calcium-bearing starting material comprises $CaCO_3$, then $CO_2$ may be generated during the method. However, wherein $CO_2$ is generated, the $CO_2$ is at a high concentration and can be stored and/or utilized.

Optionally, in any of the methods disclosed herein, the first acid comprises hydrochloric acid (HCl). Optionally, in any of the methods disclosed herein, the first acid is hydrochloric acid. Optionally, in any of the methods disclosed herein, the second acid comprises sulfuric acid ($H_2SO_4$) and/or sulfurous acid ($H_2SO_3$). Optionally, in any of the methods disclosed herein, the second acid is sulfuric acid and/or sulfurous acid. Optionally, in any of the methods disclosed herein, the second acid is sulfuric acid. Optionally, in any of the methods disclosed herein, the second acid is sulfurous acid. Optionally, in any of the methods disclosed herein, the aqueous first calcium salt is calcium chloride ($CaCl_2$)). Optionally, in any of the methods disclosed herein, the solid second calcium salt is calcium sulfate ($CaSO_4$) and/or calcium sulfite ($CaSO_3$). Optionally, in any of the methods disclosed herein, the solid second calcium salt is calcium sulfate. Optionally, in any of the methods disclosed herein, the solid second calcium salt is calcium sulfite ($CaSO_3$). Preferably, in any of the methods disclosed herein, the first cement material comprises CaO. Optionally, in any of the methods disclosed herein, the first cement material is calcium oxide (CaO). Optionally, in any of the methods disclosed herein, the first cement material is calcium oxide (CaO) or Portland cement clinker. Optionally, in any of the methods disclosed herein, the first cement material is Portland cement clinker. Optionally, in any of the methods disclosed herein, the acid-forming gas product is $SO_2$ and/or $CO_2$. Optionally, in any of the methods disclosed herein, the acid-forming gas product is $SO_2$. Optionally, in any of the methods disclosed herein, the acid-forming gas product is $CO_2$.

Preferably, but not necessarily, in any of the methods disclosed herein, the first reacting step comprises reacting the calcium-bearing starting material with hydrochloric acid to form at least aqueous calcium chloride, aqueous aluminum chloride, and solid silica. Preferably, but not necessarily, in any of the methods disclosed herein, the first separating step comprises separating a first aqueous fraction comprising the aqueous calcium chloride and the aqueous aluminum chloride from a first solid fraction comprising the solid silica. Preferably, but not necessarily, in any of the methods disclosed herein, the second reacting step comprises reacting at least the aqueous calcium chloride, the aqueous aluminum chloride, and sulfuric acid to form at least solid calcium sulfate, aqueous aluminum sulfate, and hydrochloric acid. Preferably, but not necessarily, in any of the methods disclosed herein, the thermally treating step comprises heating the calcium sulfate to form calcium oxide.

Preferably, but not necessarily, in any of the methods disclosed herein, the first reacting step comprises reacting the calcium-bearing starting material with hydrochloric acid to form at least aqueous calcium chloride, aqueous aluminum chloride, aqueous iron chloride, aqueous magnesium chloride, and solid silica. Preferably, but not necessarily, in any of the methods disclosed herein, the first separating step comprises separating a first aqueous fraction comprising the aqueous calcium chloride and the aqueous aluminum chloride from a first solid fraction comprising the solid silica. Preferably, but not necessarily, in any of the methods disclosed herein, the second reacting step comprises reacting at least the aqueous calcium chloride, and sulfuric acid to form at least solid calcium sulfate, solid calcium sulfate, and hydrochloric acid. Preferably, but not necessarily, in any of the methods disclosed herein, the thermally treating step comprises heating the calcium sulfate to form calcium oxide.

Optionally, any of the methods disclosed herein comprises an ion exchange step; wherein the ion exchange step comprises exchanging one or more anions of the first calcium salt and/or the second calcium salt for one or more hydroxyl anions to form a third calcium salt. Optionally, the ion exchange step comprises reacting the first calcium salt and/or the second calcium salt with a chelating agent to form a calcium-chelator compound and reacting the calcium-chelator compound with a base to form the third calcium salt. Optionally, the ion exchange step comprises reacting the first calcium salt and/or the second calcium salt with a base to form the third calcium salt. Optionally, the ion exchange step comprises using an ion exchange membrane to perform the exchanging one or more anions of the first calcium salt and/or the second calcium salt for one or more hydroxyl anions to form the third calcium salt. Optionally, the one or more calcium salts of the thermally treating step is the third calcium salt. Optionally, the third calcium salt is $Ca(OH)_2$. Optionally, any of the methods disclosed herein comprises a step of regenerating the chelating agent, wherein the step of regenerating the chelating agent comprises producing the third calcium salt. Optionally, any of the methods disclosed herein comprises a step of forming the first cement material from the third calcium salt. Optionally, the step of forming the first cement material from the third calcium salt comprises dehydrating the third calcium salt or directly releasing the first cement material from the calcium-chelator compound, optionally via a base. For example, CaO can be formed by using a chelating agent or base to react the $CaCl_2$), $CaSO_3$, or $CaSO_4$. For example, then the chelating agent or base can be regenerated in a manner that releases $Ca(OH)_2$ which can be dehydrated to CaO or CaO could be directly released from the chelator. For example, if $CaSO_4$ is precipitated, a chelating agent such as EDTA can be reacted with $CaSO_4$ to make Ca-EDTA. For example, a base such as NaOH can then be used to directly produce $Ca(OH)_2$ and regenerate the EDTA.

Preferably, but not necessarily, any method disclosed herein comprises a step of forming a composite cement material; wherein: (i) the thermally treating step comprises the step of forming the composite cement material and the first cement material is the composite cement material or (ii) the step of forming the composite material is performed using the first cement material formed during the thermally treating step. For example, wherein the step of forming the composite material is performed using the first cement material formed during the thermally treating step, the formation of the composite material can occur simultaneously with formation of the first cement material (e.g., CaO) or subsequently after formation of the first cement material (e.g., CaO). Optionally, any method disclosed herein comprises a step of forming a composite cement material; wherein the thermally treating step comprises the step of forming the composite cement material and the first cement material is the composite cement material. Optionally, any method disclosed herein comprises a step of forming a composite cement material; wherein the step of forming the composite material is performed using the first cement material formed during the thermally treating step. Optionally, in any of the methods disclosed herein, the step of forming the composite cement material comprises heating the second calcium salt and/or the first cement material together with one or more additives. Optionally, in any of the methods disclosed herein, the step of forming the composite cement material comprises heating the second calcium salt together with one or more additives. Optionally, in any of the methods disclosed herein, the step of forming the composite cement material comprises heating the first cement material together with one or more additives. Optionally, in any of the methods disclosed herein, the step of forming the composite cement material is performed simultaneously with the thermally treating step. Optionally, in any of the methods disclosed herein, after the thermally treating step. Optionally, in any of the methods disclosed herein, the composite cement material is Portland cement clinker. Optionally, in any of the methods disclosed herein, the composite cement material is ordinary Portland cement and/or the first cement material is calcium oxide. Optionally, in any of the methods disclosed herein, the first cement material is calcium oxide. Optionally, in any of the methods disclosed herein, the composite cement material is ordinary Portland cement. Optionally, any method disclosed herein comprises forming the one or more additives from the calcium-bearing starting material. Optionally, in any of the methods disclosed herein, the one or more additives are one or more byproducts of the first reacting step and/or are formed from one or more byproducts of the first reacting step and/or are one or more byproducts of the second reacting step and/or are formed from one or more byproducts of the second reacting step. Optionally, in any of the methods disclosed herein, the one or more additives are one or more byproducts of the first reacting step and/or are formed from one or more byproducts of the first reacting step. Optionally, in any of the methods disclosed herein, the one or more additives are one or more byproducts of the second reacting step and/or are formed from one or more byproducts of the second reacting step. Optionally, in any of the methods disclosed herein, the one or more additives are one or more byproducts of the first reacting step. Optionally, in any of the methods disclosed herein, the one or more additives are one or more byproducts of the second reacting step. Optionally, in any of the methods disclosed herein, the one or more additives are one or more byproducts of the first reacting step and/or are one or more byproducts of the second reacting step. Optionally, in any of the methods disclosed herein, a combined chemical composition of the one or more additives comprises Al and Si. Optionally, in any of the methods disclosed herein, the one or more additives are at least $Al_2O_3$ and $SiO_2$.

An advantage of the methods disclosed herein is that value-added side products can be formed. For example, instead of using simple calcium sources such as limestone or gypsum as starting materials, one can use complex minerals that include Ca and Si, and optionally other metals such as Al, Mg, and/or Fe. Instead of being undesired elements that contaminate the cement product, for example, the methods disclosed herein can include steps to form and isolate valuable products having these extra elements, such as oxides of Al, oxides of Mg, and/or oxides of Fe. These steps do not contribution significant additional operational costs.

Preferably, but not necessarily, any method disclosed herein comprises forming and isolating silica-fume grade silica, nano-silica, and/or micro-silica from the calcium-bearing starting material. Preferably, but not necessarily, any method disclosed herein comprises forming and isolating alumina from the calcium-bearing starting material.

Preferably, but not necessarily, in any method disclosed herein, the first reacting step comprises reacting the calcium-bearing starting material with hydrochloric acid to form at least aqueous aluminum chloride; wherein the method further comprises: precipitating the aluminum chloride in the presence of hydrochloric acid; and optionally reacting the precipitated aluminum chloride with sulfuric acid to form solid aluminum sulfate; heating the aluminum sulfate and/or aluminum chloride to form alumina. Preferably, but not necessarily, in any method disclosed herein, the hydrochloric acid is regenerated in these steps. Preferably, but not necessarily, in any method disclosed herein, the reaction of the precipitated aluminum chloride forms hydrochloric acid. Preferably, but not necessarily, in any method disclosed herein, the hydrochloric acid is regenerated in these steps. Preferably, but not necessarily, in any method disclosed herein, the second reacting step comprises the step of reacting the precipitated aluminum chloride. Optionally, in any of the methods disclosed herein, the thermally treating step comprises the heating the aluminum sulfate step. Optionally, in any of the methods disclosed herein, the thermally treating step comprises the heating the aluminum chloride step.

Optionally, any method disclosed herein comprises forming and isolating iron oxide from the calcium-bearing starting material. Optionally, in any of the methods disclosed herein, the forming and isolating the iron oxide comprises: forming an aqueous solution having aqueous iron sulfate and/or iron chloride and optionally at least one other metal magnesium sulfate salt and/or chloride salt formed as byproducts during the second reacting step; wherein the aqueous solution is free of a calcium salt and free of an aluminum salt; drying the aqueous solution to form solid iron sulfate and/or solid iron chloride and optionally the at least one other metal sulfate salt; heating the solid iron sulfate and optionally the at least one other metal sulfate salt to form a water-insoluble iron oxide; and optionally, dissolving the at least one other metal sulfate salt to isolate the water-insoluble iron oxide.

Optionally, any method disclosed herein comprises forming and isolating iron oxide from the calcium-bearing starting material. Optionally, in any of the methods disclosed herein, the forming and isolating the iron oxide comprises: forming an aqueous solution having aqueous iron sulfate or iron chloride and optionally at least one other metal magnesium sulfate or chloride salt formed as byproducts during the second reacting step; wherein the aqueous solution is free of a calcium salt and free of an aluminum salt; using $SO_2$ to precipitate $MgSO_3$; separating the aqueous iron salt from the solid magnesium salt; drying the aqueous solution to form solid iron sulfate or chloride and optionally the at least one other metal sulfate salt; heating the solid iron sulfate and optionally the at least one other metal sulfate salt to form a water-insoluble iron oxide; and optionally, dissolving the at least one other metal sulfate salt to isolate the water-insoluble iron oxide.

Optionally, iron chloride, iron sulfate, aluminum chloride, and/or aluminum sulfate, and/or any other iron and/or aluminum salt is produced and sold and/or combined with electrochemical strategies to make iron and aluminum metals from the aluminum chloride, sulfate, and/or other salts. For example, aluminum chloride can be isolated and aluminum can be electrowon from aluminum chloride while co-producing chlorine gas. This chlorine gas can then be reacted with hydrogen, possibly hydrogen from the cogeneration of sulfuric acid and hydrogen to regenerate HCl. Another example is iron can be electrowon from iron sulfate to regenerate sulfuric acid.

Methods disclosed herein can comprise one or more acid-forming reactions. An acid-forming reaction can be a reaction to regenerate an acid that is consumed in a different reaction of the method. The acid-forming reaction can be a reaction that supplies the acid to the (first and/or second) reacting step wherein the acid is consumed. For example, instead of supplying an acid to a reacting step, where the acid is consumed to form a calcium salt, reagents that form said acid are supplied to the reacting step such that said reacting step comprises both forming the acid and the respective acid consumption (or, salt forming) reaction.

Preferably, but not necessarily, any method disclosed herein comprises a step of forming the first acid; wherein: (i) the first reacting step comprises the step of forming the first acid and the step of forming the first acid occurs simultaneously with the first reacting step, or (ii) the step of forming the first acid is performed separately from the first reacting step. Optionally, any method disclosed herein comprises a step of forming the first acid; wherein the first reacting step comprises the step of forming the first acid and the step of forming the first acid is occurs simultaneously with the first reacting step. Optionally, any method disclosed herein comprises a step of forming the first acid; wherein the step of forming the first acid is performed separately from the first reacting step.

Preferably, but not necessarily, any method disclosed herein comprises a step of forming the second acid; wherein: (i) the second reacting step comprises the step of forming the second acid and the step of forming the second acid occurs simultaneously with the second reacting step, or (ii) the step of forming the second acid is performed separately from the second reacting step. Optionally, any method disclosed herein comprises a step of forming the second acid; wherein the second reacting step comprises the step of forming the second acid and the step of forming the second acid occurs simultaneously with the second reacting step. Optionally, any method disclosed herein comprises a step of forming the second acid; wherein the step of forming the second acid is performed separately from the second reacting step. Optionally, in any of the methods disclosed herein, the step of forming the second acid comprises reacting $SO_2$ with water to form $H_2SO_3$ and/or $H_2SO_4$; wherein the second acid is $H_2SO_3$ and/or $H_2SO_4$. Optionally, in any of the methods disclosed herein, the second acid is $H_2SO_3$ and/or $H_2SO_4$ and wherein the second calcium salt is $CaSO_3$ and/or $CaSO_4$, respectively.

Optionally, in any of the methods disclosed herein, the first acid and/or the second acid is a bulk acid. Optionally, in any of the methods disclosed herein, the first acid is a bulk acid. Optionally, in any of the methods disclosed herein, the second acid is a bulk acid.

Optionally, in any of the methods disclosed herein, the step of forming the first acid comprises forming a pH gradient via water electrolysis; wherein the first acid is formed via the water electrolysis. Optionally, in any of the methods disclosed herein, the step of forming the second acid comprises forming a pH gradient via water electrolysis; wherein the second acid is formed via the water electrolysis.

Optionally, in any of the methods disclosed herein, the second acid regeneration step according to formula FX1A is performed at a temperature selected from the range of 400 °C to 1800 °C. Optionally, in any of the methods disclosed herein, the second acid regeneration step according to formula FX1A is performed at a temperature selected from the range of 400 °C to 600 °C. Optionally, in any of the methods disclosed herein, the second acid regeneration step according to formula FX1A is performed at a temperature selected from the range of 400 °C to 600 °C, is exothermic, and is performed in the presence of a catalyst. Optionally, the catalyst comprises vanadium oxide. Optionally, in any of the methods disclosed herein, the method is characterized by a net energy selected from the range of −2 to +2 GJ per metric ton of produced cement material (e.g., produced first cement material or produced composite cement material, such as OPC). Optionally, in any of the methods disclosed herein, the method is characterized by a net energy selected from the range of −10 to +10 GJ/t, optionally −5 to +5 GJ/t, optionally −5 to +4 GJ/t, optionally −5 to +3 GJ/t, optionally −5 to +2 GJ/t, optionally −5 to +1 GJ/t, optionally −5 to +0.5 GJ/t, optionally −5 to +0.2 GJ/t, optionally −5 to +0.1 GJ/t, optionally −5 to 0 GJ/t, optionally −2 to 1 GJ/t, optionally −2 to −1.5 GJ/t, optionally −2 to +1.0 GJ/t, optionally −2 to +0.5 GJ/t, optionally −2 to +0.3 GJ/t, optionally −2 to +0.2 GJ/t, optionally −2 to +0.1 GJ/t, optionally −2 to +0 GJ/t. Optionally, in any of the methods disclosed herein, the first reacting step is exothermic. Optionally, in any of the methods disclosed herein, the second acid regeneration step is exothermic. Optionally, in any of the methods disclosed herein, the first reacting step is performed at a temperature of at least 50 °C. Optionally, in any of the methods disclosed herein, the first reacting step is performed at a temperature selected from the range of 80 °C to 100 °C, preferably 90±5 °C. Optionally, in any of the methods disclosed herein, the thermally treating step is performed at a temperature selected from the range of 1100 °C to 1800 °C. Optionally, in any of the methods disclosed herein, the thermally treating step comprises thermally treating the second calcium salt in the presence of a chemical reductant and is performed at a temperature selected from the range of 800 °C to 1200 °C. Optionally, the chemical reductant is water, carbon (or any allotrope or combination of allotropes of carbon, hydrogen gas, methane, gas, or any combination of these. Optionally, the chemical reductant is water, carbon (or any allotrope or combination of allotropes of carbon, methane, gas, or any combination of these. Optionally, the thermally treating step can be performed according to any one or a combination of formulas FX4A, FX4B, FX4C, and FX4D: $CaSO_4+H_2O \rightarrow CaO+H_2SO_4$ (FX4A); $CaSO_4+2C \rightarrow CaS+2CO_2$ (FX4B); $CaSO_4+CH_4 \rightarrow CaS+CO_2+2H_2O$ (FX4C); $CaS+3CaSO_4 \rightarrow 4CaO$ (FX4D).

Any of the methods disclosed herein can be performed as a batch process, a plug flow process, a semi-continuous process, a staged process, a continuous process, or any combination of these. Any of step of any method disclosed herein can be performed as a batch process, a plug flow process, a semi-continuous process, a staged process, a continuous process, or any combination of these.

Additional aspects of the invention disclosed herein include a method for producing a cement material via reductive thermal decomposition, the method comprising steps of: reacting a calcium-bearing material with a chemically reducing gas to produce methane and a cement material. Preferably, but not necessarily, in any method for producing a cement material via reductive thermal decomposition, the calcium-bearing material comprises $CaCO_3$, $CaSO_4$, CaS, a calcium salt, or any combination thereof. Preferably, but not necessarily, in any method for producing a cement material via reductive thermal decomposition, the calcium-bearing material is $CaCO_3$, $CaSO_4$, CaS, or any combination thereof. Preferably, but not necessarily, in any method for producing a cement material via reductive thermal decomposition, the calcium-bearing material is $CaCO_3$. Preferably, but not necessarily, in any method for producing a cement material via reductive thermal decomposition, the calcium-bearing material comprises $CaCO_3$. Preferably, but not necessarily, in any method for producing a cement material via reductive thermal decomposition, the chemically reducing gas is hydrogen gas or a gas that comprises hydrogen gas, such as forming gas. Preferably, but not necessarily, in any method for producing a cement material via reductive thermal decomposition, the cement material comprises CaO. Preferably, but not necessarily, in any method for producing a cement material via reductive thermal decomposition, the cement material is CaO. Preferably, but not necessarily, in any method for producing a cement material via reductive thermal decomposition, a molar ratio of calcium-bearing material reacting with the chemically reducing gas is 1:4 or 1:2. Optionally, in any method for producing a cement material via reductive thermal decomposition, the reacting is performed in the presence of water. Optionally, in any method for producing a cement material via reductive thermal decomposition, the reacting is performed in the absence of water. Optionally, in any method for producing a cement material via reductive thermal decomposition, the molar ratio of $CaCO_3$ reacts with hydrogen gas at a molar ratio of 1:4 during the step of reacting. Optionally, in any method for producing a cement material via reductive thermal decomposition, the molar ratio of $CaCO_3$ reacts with hydrogen gas at a molar ratio of 1:2 during the step of reacting. Generally, the reaction according to a 1:4 molar ratio is lower energy but high OpEx because more $H_2$ needs to be made, but a lower temp can be used. Generally, the reaction according to a 1:2 molar ratio has a higher energy but lower OpEx. Optionally, in any method for producing a cement material via reductive thermal decomposition, oxygen gas, water, or a combination of oxygen gas and water is produced during the step of reacting. Optionally, any method for producing a cement material via reductive thermal decomposition comprises a step of decomposing the methane to produce hydrogen gas and one or more carbon materials. Optionally, in any method for producing a cement material via reductive thermal decomposition, the method does not comprise forming $CO_2$. Optionally, in any method for producing a cement material via reductive thermal decomposition, the step of reacting is characterized by a lower heating value (LHV) of 720 kJ/mol or less and a high heating value (HHV) of 800 kJ/mol or less. Optionally, in any method for producing a cement material via reductive thermal decomposition, the step of reacting is performed at a temperature of at least 700 °C.

Additional aspects of the invention disclosed herein include methods for producing a cement material according to a single-acid approach, wherein only one acid or only one acid reaction step is needed. In an aspect, a method of producing a cement material comprises steps of: first reacting a calcium-bearing starting material with a first acid to produce a first aqueous fraction comprising an aqueous first calcium salt and a first solid fraction comprising one or more solid byproducts; wherein: the calcium-bearing starting material has a chemical composition comprising a plurality of metal elements including at least Ca and Si; the one or more solid byproducts comprises a silicon salt; first separating the first aqueous fraction from the first solid fraction; and treating the first calcium salt to produce a first cement material. Optionally, the treating step comprises thermally treating (or, thermally decomposing) the first calcium salt in the presence of water to produce the first cement material. Optionally, thermally treating (or, thermally decomposing) the first calcium salt regenerates the first acid. Optionally, the treating step comprises an ion exchange step; wherein the ion exchange step comprises exchanging the one or more anions of the first calcium salt for one or more hydroxyl anions to form a third calcium salt. Optionally, the ion exchange step comprises reacting the first calcium salt with a chelating agent to form a calcium-chelator compound and reacting the calcium-chelator compound with a base to form the third calcium salt. Optionally, the ion exchange step comprises reacting the first calcium salt with a base to form the third calcium salt. Optionally, the ion exchange step comprises using an ion exchange membrane to perform the exchanging one or more anions of the first calcium salt for hydroxyl anions to form the third calcium salt. Preferably, the third calcium salt is $Ca(OH)_2$. Optionally, the treating step comprises thermally treating (or, thermally decomposing) the third calcium salt to produce the first cement material. Optionally, the base is a hydroxide compound. Optionally, the first calcium salt is $CaCl_2$). Optionally, for example, the treating step comprises thermally decomposing $CaCl_2$) in presence of air according to formula: $CaCl_2+O_2 \rightarrow CaO+Cl_2+\frac{1}{2}O_2$. Optionally, for example, the treating step comprises thermally treating $CaCl_2$ in the presence of water according to formula: $CaCl_2+H_2O \rightarrow CaO+2HCl$. Optionally, for example, the treating step comprises ion exchange using an ion exchange membrane to exchange CI ions for OH ions thereby forming $Ca(OH)_2$. Optionally, the treating step further comprises dehydrating the $Ca(OH)_2$ to make the first cement material. Optionally, for example, the treating step comprises reacting the first calcium salt with a chelating agent to form a calcium-chelator compound. Optionally, for example, the treating step comprises reacting a base such as NaOH, $Mg(OH)_2$, or MgCl(OH), with the first calcium salt, such as $CaCl_2$ to form $Ca(OH)_2$. Optionally, for example, the treating step further comprises thermally decomposing $Ca(OH)_2$ to make the first cement material. The first cement material optionally is or optionally comprises CaO. Optionally, the first acid is hydrogen chloride. Optionally, the one or more solid byproducts comprise $SiO_2$. Optionally, the at least one multinary metal oxide material is at least one natural rock or mineral.

Optionally, in any of the methods disclosed herein, the first calcium salt and/or the second calcium salt is other than $Ca(OH)_2$ or comprises a salt other than $Ca(OH)_2$. Optionally, in any of the methods disclosed herein, the first reacting step is not an electrochemical step. Optionally, in any of the methods disclosed herein, the second reacting step is not an electrochemical step. Optionally, in any of the methods disclosed herein, the calcium-bearing starting material is other than $CaCO_3$ or comprises a material other than $CaCO_3$.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

STATEMENTS REGARDING CHEMICAL COMPOUNDS AND NOMENCLATURE

Figure 1:
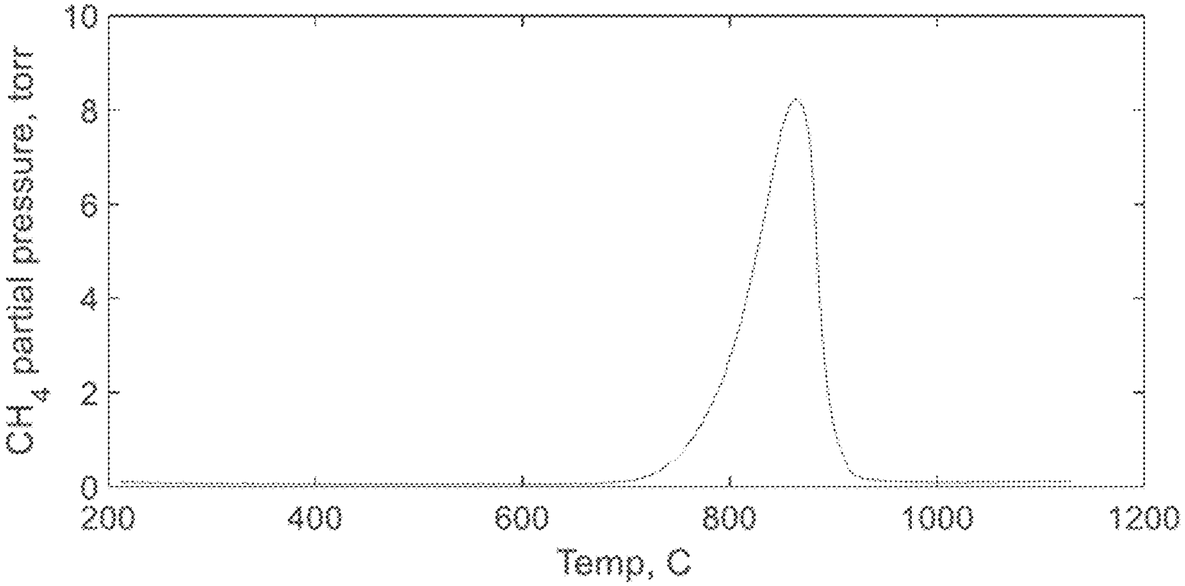
FIG. 1. A plot showing methane production in a tube furnace in partial pressure of methane versus temperature. 0.3 lpm of forming gas (5% $H_2$, 95% $N_2$) flow rate.

In general, the terms and phrases used herein have their art-recognized meaning, which can be found by reference to standard texts, journal references and contexts known to those skilled in the art. The following definitions are provided to clarify their specific use in the context of the invention.

The terms "thermal conversion" and "thermally converting" refer to the conversion of a first chemical species to a second chemical species via a thermally-activated or thermally-driven process, which may also be referred to as a thermochemical process. An exemplary process for thermal conversion of a chemical species is burning, though thermal conversion processes are not necessarily limited thereto. For example, thermal conversion of sulfur to sulfur dioxide may include burning of the sulfur, such as via a sulfur burner system. Thermal oxidation of a species is a form of thermal conversion of the species. For example, thermal conversion of sulfur to sulfur dioxide may be referred to as thermal oxidation of the sulfur to sulfur dioxide. In some embodiments, thermal conversion may be aided by a catalyst. In some embodiments, thermal conversion does not require a catalyst or is performed without a catalyst. It should be noted that thermal oxidation and electrochemical oxidation are different processes, where thermal oxidation is driven or activated thermally (via heat or burning) and electrochemical oxidation is driven electrochemically (e.g., via applying or withdrawing electrical energy, optionally with the aid of an electrochemical catalyst). The term "thermally treating" refers thermal treatment or exposure to heat, preferably in excess of room temperature heat, of one or more materials (such as a calcium salt, such as $CaSO_4$) such that the one or more material may thermally convert, thermally decompose, or otherwise experience a heat-induced chemical change into another material (such as a cement material, such as CaO). For example, calcium sulfate (gypsum) may thermally convert/decompose into calcium oxide (CaO), along with formation of byproducts such as $SO_2$ and oxygen. A thermal treatment may also cause a plurality of materials, such as a plurality of materials comprising calcium, aluminum, and silicon, to convert into or otherwise form a composite cement material, such as Ordinary Portland Cement (OPC).

The term "calcium-bearing starting material" refers to one or more materials the chemical composition of which comprises Ca. A calcium-bearing starting material can be a single material, such as a mineral whose chemical composition includes the element Ca, such as in the form of Ca cations as part of an ionic material, such as a multinary metal oxide material. A calcium-bearing starting material can be a plurality of materials, such as one or more rocks, minerals, and/or industrially-processed material, wherein the chemical composition of the combination of said plurality of materials includes the element Ca, such as in the form of Ca cations of an ionic material, such as a multinary metal oxide material. Wherein a calcium-bearing starting material is a plurality of materials, any one or any combination of said plurality of materials can have a chemical composition comprising the element Ca in order for the chemical composition of the combination of said plurality of materials (which together are the calcium-bearing starting material) to include the element Ca. Preferably, a calcium-bearing starting material having a chemical composition comprising the element Ca refers to the weight percent and/or the molar percent of Ca in said calcium-bearing starting material being at least 0.001%, preferably at least 0.01%, preferably at least 0.1%, more preferably at least 1%, further more preferably at least 5%, still more preferably at least 10%, and yet more preferably at least 20%. On the other hand, the methods disclosed herein are compatible with a calcium-bearing starting material whose chemical composition has a low weight percent and/or molar percent, such as less than 60%, less than 55%, less than 50%, less than 45%, less than 40%, and less than 20%, at least because Ca, along with respective counterions, can be isolated.

Generally, material or species having a chemical composition characterized as comprising an element X (wherein "X" is an element of the Periodic Table of Elements) refers to the weight percent and/or the molar percent of X in said material or species being at least 0.001%, preferably at least 0.01%, more preferably at least 0.1%, and still more preferably at least 1%.

The term "calcium salt" refers to a salt whose chemical composition comprises the element Ca, for example in the form of Ca cations. A salt is a chemical compound comprising ionic species associated with each other at least in part via ionic bonding. For example, $CaSO_4$ and $CaCl_2$) are calcium salts wherein Ca is a cation and $SO_4$ and CI, respectively, are anions.

A regeneration step refers to a step of a process for producing a species or material using a product of a different step that consumes (e.g., converted via chemical change into another species or material) in said species or material. For example, a reaction characterized by ($A+B \rightarrow C+D$) consumes species A and B to form species C and D. A reaction characterized by ($C+E \rightarrow A+F$) can be referred to as a regeneration reaction for regenerating species A using a product (species C) of the reaction that consumed species A.

The term "solid fraction" refers to solid species present in a mixture of solid(s) and liquid(s). The term "liquid fraction" refers to liquid species and species dissolved in the liquid species in a mixture of solid(s) and liquid(s). For example, a solid fraction can have the solid products of a chemical reaction and liquid fraction can have the liquid and dissolved products of the chemical reaction. Each of the solid fraction and the liquid fraction can optionally include unreacted reagents. The liquid fraction can include solvent(s) and ions dissolved in said solvent(s).

A "dry mass" of one or more materials, such as a solid fraction, refers to the mass of the one or more materials being free of water, and optionally free of any liquid species.

The term "metal oxide" generally refers to a material whose chemical composition comprises one or more metal elements and the element O. Optionally, a metal oxide material is an ionic material or at least partially an ionic material wherein at least a fraction of the chemical bonding is characterized as ionic bonding. A metal element is any metal element or metalloid element of the periodic table of elements. Generally, a metalloid element is selected from the group consisting of B, Si, Ge, As, Se, Sb, Te, Po, and At.

The term "natural rock or mineral" refers to one or more materials that is naturally found in and has been extracted from the Earth's crust. Natural rocks and minerals include, but are not limited to, basalt, igneous appetites, wollastonite, anorthosite, montmorillonite, bentonite, calcium-containing feldspar, anorthite, diopside, pyroxene, pyroxenite, mafurite, kamafurite, clinopyroxene, colemonite, grossular, augite, pigeonite, margarite, calcium serpentine, garnet, scheilite, skarn, limestone, natural gypsum, appetite, fluorapatite, and any combination of these. In contrast, cement, concrete, Portland cements, fly ash, and slag are not natural rocks or mineral but may be referred to as industrially-derived materials.

The term "bulk acid" refers to an acid or acid solution that does not require continuous input of energy (such as electrical energy) and/or exchange of electrons with an electrode surface to exist and function as required by a given process or step thereof. In contrast, a heterogeneous or local acidic solution, such as of hydronium ions or protons, near an electrode and formed as a result of and substantially only during exchange of electrons between the electrode and the solution is not a bulk acid. For example, a bulk acid is not a heterogeneous or local or acidic solution corresponding to a pH gradient formed at an electrode during water electrolysis. In certain embodiments, the term "bulk acid" refers to an acid or acid solution that exhibits thermodynamic, chemical, and/or kinetic stability on a time scale of at least 10 seconds, preferably at least 1 minute, in the absence of electrical energy input. In certain embodiments, the term "bulk acid" refers to an acid or acid solution that does exhibit or is capable of exhibiting thermodynamic, chemical, and/or kinetic stability on a time scale of at least 1 seconds and a length scale of at least 10 cm, preferably at least 10 cm from a surface of a bulk material, in the absence of electrical energy input.

The term "electrochemical cell" refers to devices and/or device components that perform electrochemistry. Electrochemistry refers to conversion of chemical energy into electrical energy or electrical energy into chemical energy. Chemical energy can correspond to a chemical change or chemical reaction. Electrochemistry can thus refer to a chemical change (e.g., a chemical reaction of one or more chemical species into one or more other species) generating electrical energy and/or electrical energy being converted into or used to induce a chemical change. Electrical energy refers to electric potential energy, corresponding to a combination of electric current and electric potential in an electrical circuit. Electrochemical cells have two or more electrodes (e.g., positive and negative electrodes; e.g., cathode and anode) and one or more electrolytes. An electrolyte may include species that are oxidized and species that are reduced during charging or discharging of the electrochemical cell. Reactions occurring at the electrode, such as sorption and desorption of a chemical species or such as an oxidation or reduction reaction, contribute to charge transfer processes in the electrochemical cell. Electrochemical cells include, but are not limited to, electrolytic cells such as electrolysers and fuel cells. Electrochemical oxidation may occur at the positive electrode, for example, and electrochemical reduction may occur at the negative electrode, for example. Electrochemical oxidation refers to a chemical oxidation reaction accompanied by a transfer of electrical energy (e.g., electrical energy input driving the oxidation reaction) occurring in the context an electrochemical cell. Similarly, electrochemical reduction refers to a chemical reduction reaction accompanied by a transfer of electrical energy occurring in the context an electrochemical cell. A chemical species electrochemically oxidized during charging, for example, may be electrochemically reduced during discharging, and vice versa. The term "electrochemically" or "electrochemical" may describe a reaction, process, or a step thereof, as part of which chemical energy is converted into electrical energy or electrical energy is converted into chemical energy. For example, a product may be electrochemically formed when electrical energy is provided to help the chemical conversion of a reactant(s) to the product proceed. The term "non-electrochemical" refers to a reaction or process that does not include electrochemistry and/or does not require electrochemistry in order to be performed.

A reacting step refers to a process step wherein a chemical reaction occurs, characterized by one or more chemical species experiencing a chemical change (such as via chemically reacting with each other) into another one or more chemical species.

The term "elemental sulfur" refers to any one or combination of the allotropes of sulfur, such as, but not limited to, $S_7$, $S_8$, $S_6$, $S_{12}$, and $S_{18}$, and including crystalline, polycrystalline, and/or amorphous sulfur.

"RHE" refers to the reference electrode commonly referred to as the reversible hydrogen electrode. "SCE" refers to the reference electrode commonly referred to as the saturated calomel electrode.

The term "initial hours of operation" refers to the time during which the cell is operational starting from the very first/initial operation, or "turning on," of the cell. Time during which the cell or system is not being operated (i.e., no electrochemical reduction or oxidation occurring therein, or no electrical energy input or output is occurring) is not included in the initial hours of operation determination.

In some embodiments, the term "aqueous" refers to a solution where the solvent is water such that other species of the solution, or solutes, are substantially solvated by water. In some embodiments, the term "aqueous" may generally refer to a solution comprising water. Optionally, but not necessarily, an aqueous solution or an aqueous solvent includes 5 vol. % or less of non-aqueous solvent and/or solute species.

The term "amending agricultural water" refers to changing or adding something, such as a solute, to agricultural water. For example, acidification of agricultural water by the addition of sulfuric acid, such as a solution including sulfuric acid, to agricultural water. Agricultural water refers to water used for an agricultural purpose, such as irrigation. The term "amending soil" refers to changing or adding something to soil. For example, acidification of soil by the addition of sulfuric acid, such as a solution including sulfuric acid, to soil.

The term "cement" refers to hydraulic, non-hydraulic, or both hydraulic and non-hydraulic cement material. An exemplary cement is, but is not limited to, Portland cement. Generally, a cement is a binder material, which, for example, may be mixed with fine aggregate particles (such as to produce mortar for masonry) or with sand and gravel (to produce concrete). According to certain embodiments, cement comprises calcium oxide. Cement may optionally further comprise one or more other materials including, but not limited to, certain silicate(s), $SiO_2$, certain oxide(s), $Fe_2O_3$, certain aluminate(s), $Al_2O_3$, belite, alite, tricalcium aluminate, brownmillerite, A "cement material" refers to a material that is or can be a constituent of cement. Preferably, a cement material has a chemical composition comprising Ca or CaO. For example, CaO is a cement material. For example, a cementitious material is a cement material. A composite cement material may include a plurality of materials, including at least one cement materials and optionally one or more additives. Exemplary composite cement materials are, but are not limited to, Portland cement clinker and Portland cement, such as Ordinary Portland Cement (OPC).

The term "substantially" refers to a property or condition that is within 20%, optionally within 10%, optionally within 5%, optionally within 1%, or optionally is equivalent to a reference property or condition. The term "substantially equal," "substantially equivalent," or "substantially unchanged," when used in conjunction with a reference value describing a property or condition, refers to a value or condition that is within 20%, optionally within 10%, optionally within 5%, optionally within 1%, optionally within 0.1%, or optionally is equivalent to the provided reference value or condition. For example, a voltage that is substantially 500 mV (or, substantially equivalent to 500 mV) is within 20%, optionally within 10%, optionally within 5%, optionally within 1%, or optionally equal to 500 mV. The term "substantially greater," when used in conjunction with a reference value or condition describing a property or condition, refers to a value that is at least 2%, optionally at least 5%, optionally at least 10%, or optionally at least 20% greater than the provided reference value or condition. For example, a voltage is substantially greater than 500 mV if the voltage is at least 20% greater than, optionally at least 10% greater than, optionally at least 5% greater than, or optionally at least 1 greater than 500 mV. The term "substantially less," when used in conjunction with a reference value or condition describing a property or condition, refers to a value or condition that is at least 2%, optionally at least 5%, optionally at least 10%, or optionally at least 20% less than the provided reference value. For example, a voltage is substantially less than 500 mV if the voltage is at least 20% less than, optionally at least 10% less than, optionally at least 5% less than, or optionally at least 1% less than 500 mV.

Further, incorporated herein by reference, to the extent not inconsistent herewith, is U.S. Patent Publication No. 2019/0376191 (Finke; U.S. application Ser. No. 16/415,275), which may contain additional useful terms, descriptions, and embodiments.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

The invention can be further understood by the following non-limiting examples.

Example 1: A Process to Make Calcium Oxide or Ordinary Portland Cement from Calcium Bearing Rocks and Minerals Conventional cement is made by thermally decomposing $CaCO_3$ into CaO and then mixing it with other materials including $Al_2Si_2O_5(OH)_4$, $Fe_2O_3$, and $CaSO_4$. Thermal decomposition occurs at ~900C and final OPC production occurs at ~1450C. Most of the energy required and $CO_2$ emissions for cement making come from the thermal decomposition of limestone:

$$CaCO_3 \rightarrow CaO + CO_2 \Delta H = 178 \text{(non spontaneous)} \quad \text{(FX5).}$$

Conventional cement requires 2.7-6 GJ/tonne OPC and produces 0.7-1.3 tonne $CO_2$ per tonne of OPC (Ordinary Portland Cement). The normal cement process emits a lot of $CO_2$ and take a lot of energy.

Included in this discloses is a process to produce CaO from any calcium-bearing rock or mineral. In nature, acid (e.g. $H_2CO_3$ or $H_2SO_4$) weathers calcium bearing minerals to produce, typically, $CaCO_3$ or $CaSO_4$. The general weathering trend follows:

$$H_2CO_3 + CaAl_2Si_2O_8 + H_2O \rightarrow CaCO_3 + Al_2Si_2O_5(OH)_4 \quad \text{(FX6);}$$

or $$H_2SO_4 + CaAl_2Si_2O_8 + H_2O \rightarrow CaSO_4 + Al_2Si_2O_5(OH)_4 \quad \text{(FX7).}$$

In nature, these acids are very dilute and typically this weathering occurs over long periods of time (weeks to decades). Weathering can occur with a calcium bearing mineral or rock. Common examples are wollastinite, anorthocite, Ca-bentonite, montmorillonite, plagioclase and basalt. All calcium bearing rocks are possible including all mafic and ultra-mafic rocks.

Methods disclosed herein can use an acid (e.g. $H_2SO_4$, HF, HCl, $H_2CO_3$) or a combination of acids plus a calcium bearing rock or mineral (e.g. anorthosite, montmorillonite, wollastonite) to produce a calcium salt (e.g. $CaSO_4$, $CaF_2$, $CaCl_2$), $CaCO_3$). It is then possible to hydrate or thermally decompose this salt to produce CaO. It may also be possible to achieve the correct ratios of starting materials to thermally decompose the calcium salt and byproducts into a cementitious material including Ordinary Portland Cement or calcium sulfoaluminate cement. The strength, concentration, or quality of the acid and the particle size of the mined calcium-bearing rock can change the kinetics of the removal of calcium salts from the calcium-bearing starting material and different acid concentrations and crushed rock sizes may be optimal for different versions of this process.

The advantages of the processes disclosed herein can include that they can be $CO_2$ free and energy neutral. For example:

$$H_2SO_4+CaAl_2Si_2O_8+H_2O\rightarrow CaSO_4+Al_2Si_2O_5(OH)_4 \quad (FX8);$$

$$CaSO_4\rightarrow CaO+SO_2+\tfrac{1}{2}O_2 \quad (FX9);$$

$$SO_2+H_2O+\tfrac{1}{2}O_2\rightarrow H_2SO_4 \quad (FX10);$$

$$\text{Net: } CaAl_2Si_2O_8+2H_2O\rightarrow CaO+Al_2Si_2O_5(OH)_4 \quad (FX11);$$

$$\Delta H = \sim 0$$

This process could also be used to make clean hydrogen if electrochemical cogeneration of $H_2$ and $H_2SO_4$ are used:

$$H_2SO_4+CaAl_2Si_2O_8+H_2O\rightarrow CaSO_4+Al_2Si_2O_5(OH)_4 \quad (FX12);$$

$$CaSO_4\rightarrow CaO+SO_2+\tfrac{1}{2}O_2 \quad (FX13);$$

$$SO_2+2H_2O\rightarrow H_2+H_2SO_4 \quad (FX14);$$

$$\text{Net: } CaAl_2Si_2O_8+2H_2O\rightarrow CaO+Al_2Si_2O_5(OH)_4+\tfrac{1}{2}O_2+H_2 \quad (FX15);$$

$$\Delta H=50 \text{(slightly uphill)}$$

Example 2: Reductive Thermal Decomposition of Limestone to Make Lime or Cement Lime is used directly as a commodity chemical as well as the primary constituent of cement which is the most consumed human made material on the planet. Lime is currently produced via the thermal decomposition of limestone in an air atmosphere (FX16).

$$CaCO_3\rightarrow CO_2+CaO \quad (FX16);$$

This heat of decomposition of this reaction is 178 kJ/mol

Included in this invention is a process to produce cement from limestone via reductive thermal decomposition with hydrogen. The first step in the process may follow the following reactions:

$$CaCO_3+4H_2\rightarrow CH_4+2H_2O \quad (FX17A);$$

or $$CaCO_3+2H_2\rightarrow CH_4+O_2 \quad (FX17B);$$

Water content of the reacting gas influences whether the reaction proceeds according to FX17A, FX17B, or both. $CaCO_3$ can react with $H_2$ to either make $CaO+CH_4+O_2$ or $CaO+CH_4+2H_2O$. If $H_2O$ is formed, 4 $H_2S$ are consumed. If $O_2$ is formed, only 2 $H_2S$ are consumed. This reaction can be driven to only consume 2 $H_2S$ if there is a water atmosphere, for example.

The reaction may stop there or the second step may be methane pyrolysis to regenerate the hydrogen, or any methane involving chemical reaction:

$$CH_4\rightarrow 2H_2+C \quad (FX18);$$

One benefit of this reaction is that we can make solid carbon instead of $CO_2$ and therefore will not pollute the atmosphere. Another benefit of reaction FX17A is that it is a lower energy requirement than traditional thermal decomposition of limestone (13.1 kJ/mol). A benefit of reaction FX17B is that 100% of the necessary hydrogen can be regenerated from methane pyrolysis.

Figure 2:
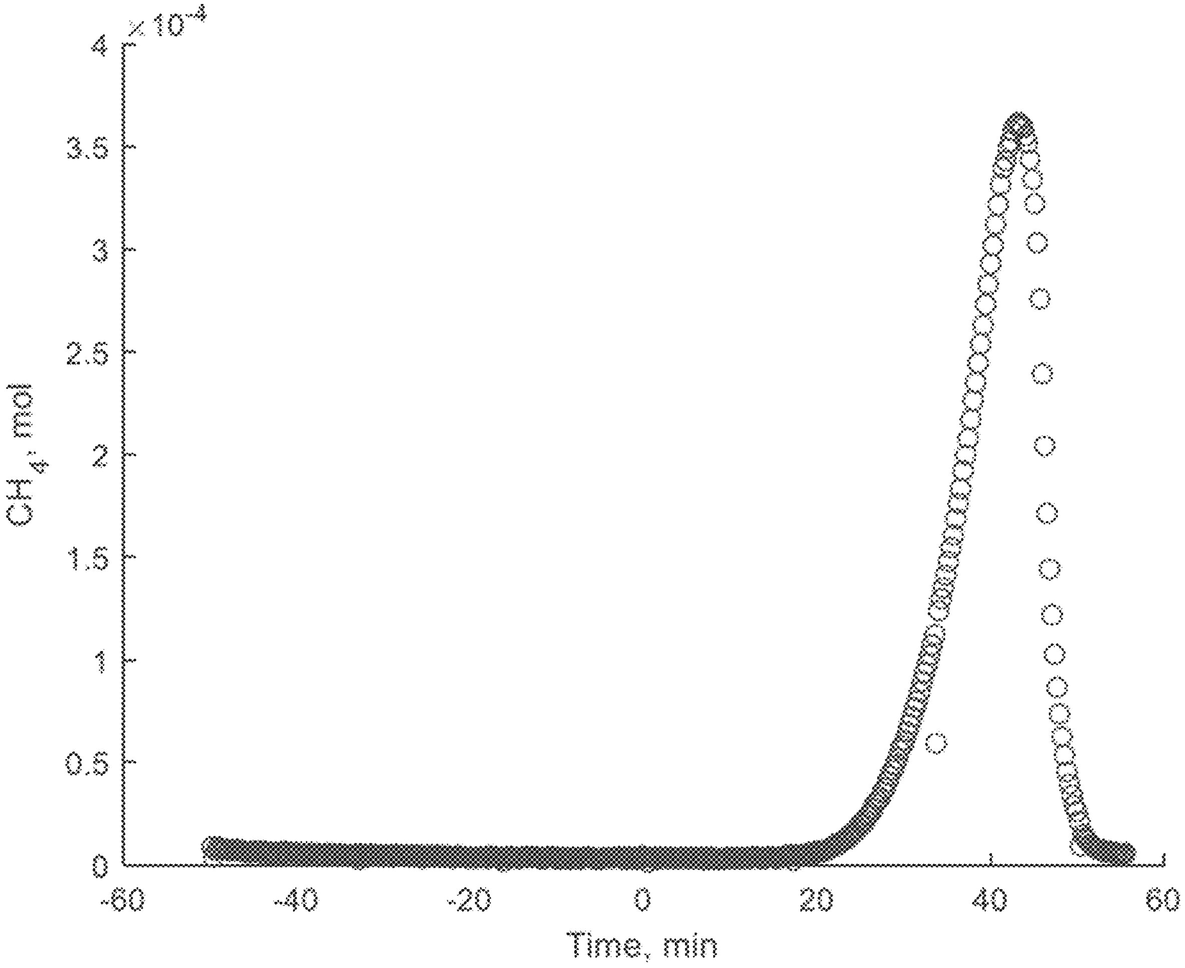
FIG. 2. A plot showing methane production in a tube furnace in mole methane versus time. 0.3 lpm of forming gas (5% $H_2$, 95% $N_2$) flow rate.
Figure 3:
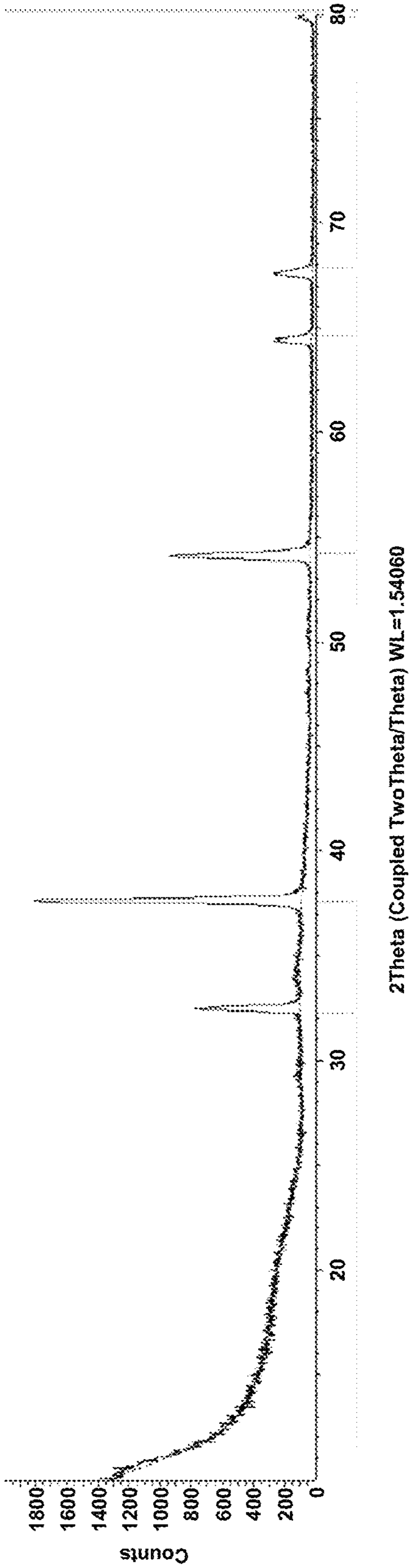
FIG. 3. An XPS pattern of a product obtained from reacting $CaCO_3$ in a reducing environment illustrating the pure CaO appears to be produced.

In certain embodiments, reaction FX17A occurs under reducing conditions above 700C for example in an $H_2$, an $H_2/N_2$ atmosphere or any other combination. Reaction FX17B may occur above 700C with $H_2$ under a water atmosphere. For example, we put 2.011 g of $CaCO_3$ powder into a tube furnace and heated it at 7 C per minute. For example, we flowed forming gas at 0.3 liters per minute (lpm). For example, we attached a gas analyzer to the back of the furnace to measure the methane concentration. Data is found in FIGS. 1 and 2. XPS is to determine that the resulting thermal decomposition yielded >99% lime (FIG. 3).

By integrating under these curves, we determine that we achieved ~100% decarbonization.

Example 3: Production of Gypsum and Cement Materials

Exemplary aspect 1: The production of ordinary portland cement (OPC) from any calcium containing starting material without the net production of acid-forming gases (e.g. $SO_2$ and $CO_2$). Examples of calcium containing starting materials include: basalt, igneous appetites, wollastonite, slag, fly ash, anorthosite, montmorillonite, bentonite, calcium-containing feldspar, anorthite, diopside, pyroxene, pyroxenite, mafurite, kamafurite, clinopyroxene, colemonite, grossular, augite, pigeonite, margarite, calcium serpentine, garnet, scheilite, OPC, concrete, any rock that has any Ca or CaO by mass especially rocks with >5%, >10%, or >15% CaO, any skarns, limestone, gypsum, appetite, or fluorapatite.

In certain embodiments, we do this by first producing >90% pure synthetic gypsum from the above calcium containing rocks (details in claim 2) and then thermally decomposing this gypsum to make CaO and then mixing it with the proper ratios of other materials to form OPC. The produced $SO_2$ is then reformed into sulfuric acid (via the contact process or via a sulfur depolarization electrolyzer) which can then be recycled to make synthetic gypsum. The general chemistry is below:

1. $CaAl_2Si_2O_8+H_2SO_4\rightarrow CaSO_4(>90 \text{ dry wt. \% pure})+Al_2O_3+SiO_2$ (FX19);
2. $CaSO_4+\text{heat}\rightarrow CaO+\tfrac{1}{2}O_2+SO_2$ (FX20);
3. $CaO+xAl_2O_3+ySiO_2\rightarrow OPC$ (FX21);
4. $SO_2+\tfrac{1}{2}O_2+H_2O\rightarrow H_2SO_4$ (FX22);

Ordinary Portland Cement (OPC) is made in industry today exclusively from limestone (primarily $CaCO_3$). The production of OPC involves first producing CaO by thermally decomposing $CaCO_3$ (e.g. $CaCO_3+\text{heat}\rightarrow CaO+CO_2$) and then heating the CaO with silica and alumina to form OPC which is ~60% CaO by mass. The production of $CO_2$ from cement manufacturing is responsible for >5% of global $CO_2$ emissions.

Besides limestone, OPC may also be made from gypsum ($CaSO_4$). Mined gypsum ($CaSO_4$) can be used by some methods for producing OPC. In this process $CaSO_4$ is thermally decomposed to produce CaO (e.g. $CaSO_4+\text{heat}\rightarrow CaO+\tfrac{1}{2}O_2+SO_2$). This process can also be accomplished with carbo or hydro thermic reduction in which case CaS is produced by reacting $CaSO_4$ with a reductant (e.g.

coal) and then CaS is co-thermally-decomposed with $CaSO_4$ to make CaO. This process is known as the Mueller-Kuehne Process. Neither of these processes are practiced commercially today because $SO_2$ cannot be released into the atmosphere and the global demand for $SO_2$ is far lower than the demand for OPC.

OPC can be produced from "phosphogypsum" ($CaSO_4$ produced by reacting phosphate rock with $H_2SO_4$ to make phosphoric acid and gypsum). The fertilizer industry produces waste $CaSO_4$ by reacting sulfuric acid with phosphate rock (primarily $Ca_5(PO_4)_3OH$) to make phosphoric acid. This synthetic gypsum can be thermally decomposed to make CaO and then OPC as in the process above.

Methods disclosed herein dramatically expand the starting materials from which OPC can be made compared to conventional methods.

Exemplary Aspect 2: The production of >90% purity $CaSO_4$ from any calcium containing rock. For example, HCl is first reacted with the rock to dissolve the calcium chloride, precipitates out >90 dry wt % purity SiO2, and other byproducts. For example, we then react the dissolved solution with sulfuric acid which selectively precipitates out $CaSO_4$ as this is the only sulfate salt among the common sulfate salts ($MgSO_4$, $Al_2(SO_4)_3$, $Fe_2(SO_4)_3$) that does not dissolve in water. This also regenerates the HCl. Sample chemistry is below:

1. $CaAl_2Si_2O_8+8HCl \rightarrow CaCl_{2(aq)}+2AlCl_{3(aq)}+SiO_{2(s)}$ (FX23);

2. Separate the solid and aqueous fraction (FX24);

3. $CaCl_{2(aq)}+2AlCl_{3(aq)}+4H_2SO_4 \rightarrow CaSO_{4(s)}+Al_2(SO_4)_{3(aq)}+8HCl$ (FX25);

Methods disclosed herein include production of >90 dry wt. % purity $CaSO_4$, which is make the process less expensive, less complicated, more controllable of necessary materials ratios for accurate production of OPC.

90 dry wt. % calcium sulfate can also be produced as a byproduct of reacting sulfuric acid with either limestone ($CaCO_3$) and phosphate rock ($Ca_5(PO_4)_3OH$ or $Ca_5(PO_4)_3F$). The products of these reactions are either water soluble (HF, $H_2PO_4$), liquid ($H_2O$) or gaseous ($CO_2$).

Advantageously, methods disclosed herein can yield highly pure synthetic gypsum from any rock even if the byproducts are not soluble in sulfuric acid.

Example 4: Generation of Valuable Co-Products

Exemplary aspect 3: The production of alumina from any calcium containing rock. This can be done by first leaching with HCl and then saturating the leach solution with HCl, the high HCl concentration causes $AlCl_3$ to precipitate. $AlCl_3$ can then be mixed with $H_2SO_4$ to make $Al_2(SO_4)_3$ and regenerate the HCl. $Al_2(SO_4)_3$ can be thermally decomposed to make $Al_2O_3$ and make $SO_2$ in order to regenerate the sulfuric acid. Exemplary chemistry below:

1. $CaAl_2Si_2O_8+8HCl \rightarrow CaCl_{2(aq)}+2AlCl_{3(aq)}+SO_{2(s)}$ (FX26);

2. $AlCl_{3(aq)}+HCl_{(aq)} \rightarrow AlCl_{3(s)}+HCl_{(aq)}$ (FX27);

3. $2AlCl_{3(s)}+H_2SO_4 \rightarrow Al_2(SO_4)_3$ (FX28);

4. $Al_2(SO_4)_3+heat \rightarrow 3SO_2+Al_2O_3+3/2O_2$ (FX29);

5. $SO_2+1/2O_2+H_2O \rightarrow H_2SO_4$ (FX30);

Exemplary aspect 4: The production of iron oxide from any calcium containing rock. Once Al, Ca, and Si are removed via the process described above, only aqueous iron sulfate and magnesium sulfate are left in solution. If the water is evaporated and the salts are raised to 500-700C iron sulfate will decompose into insoluble iron oxide and the remaining magnesium sulfate can be dissolved away in water leaving only iron oxide.

Exemplary aspect 5: The production of supplementary cementitious materials including silica fume from calcium-containing rocks. A side benefit of our process is that because it dissolves everything except the silica, the particle size of everything is very small and therefore we can make synthetic silica fume.

The production of value added co-products is a significant advantage of methods disclosed herein. An unexpected added benefit of the leach step(s), corresponding to the "first reacting" step, or the reaction of a calcium-bearing starting material with a first acid, is it can produce numerous co-products including $Al_2O_3$, $SiO_2$, silica-fume grade silica, $Fe_2O_3$, and MgO. These products also may be highly pure because a chemical separation is used. The use of HCl concentration to precipitate aluminum had been used to make $AlCl_3$ from aluminum containing rocks but not to make $Al_2(SO_4)_3$, as disclosed herein, according to certain embodiments, which has the benefit of higher thermal decomposition efficiencies and the regeneration of valuable HCl.

Methods disclosed herein include benefits of expanding the starting materials that are capable of making these products, and, in many cases, achieving better processes efficiencies, product purities, and qualities than conventional processes.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every device, system, formulation, composition, combination of components, or method, or step thereof, described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method comprising:

reacting a calcium-bearing starting material with an aqueous solution to produce a first aqueous fraction comprising an aqueous calcium salt and a first solid fraction comprising one or more solid byproducts; wherein:

the calcium-bearing starting material has a chemical composition comprising a plurality of metal elements including at least Ca and Si; and the one or more solid byproducts comprises a silicon compound;

separating the first aqueous fraction from the first solid fraction; and treating the calcium salt to produce a cement material;

wherein the cement material comprises CaO.

2. The method of claim 1, further comprising thermally treating the calcium-bearing starting material before reacting.

3. The method of claim 2, wherein the thermal treatment is performed in the presence of an additive.

4. The method of claim 1, further comprising treating the first aqueous fraction with a base after separating the first aqueous fraction from the first solid fraction.

5. The method of claim 1, wherein the aqueous solution comprises an acid.

6. The method of claim 5, wherein the acid comprises hydrochloric acid.

7. The method of claim 5, wherein the acid is a bulk acid.

8. The method of claim 1, wherein the calcium-bearing starting material comprises at least one multinary metal oxide material having a composition comprising Ca and at least one other metal element selected from the group consisting of Al, Si, Fe, Mn, and Mg.

9. The method of claim 1, wherein the calcium-bearing starting material comprises at least one natural rock or mineral comprising basalt, igneous appetites, wollastonite, anorthosite, montmorillonite, bentonite, calcium-containing feldspar, anorthite, diopside, pyroxene, pyroxenite, mafurite, kamafurite, clinopyroxene, colemonite, grossular, augite, pigeonite, margarite, calcium serpentine, garnet, scheilite, skarn, limestone, natural gypsum, appetite, fluorapatite, or any combination of these.

10. The method of claim 9, wherein the calcium-bearing starting material comprises at least one natural rock or mineral comprising basalt, igneous appetites, wollastonite, anorthosite, montmorillonite, bentonite, calcium-containing feldspar, anorthite, diopside, pyroxene, pyroxenite, mafurite, kamafurite, clinopyroxene, colemonite, grossular, augite, pigeonite, margarite, calcium serpentine, garnet, scheilite, skarn, natural gypsum, appetite, fluorapatite, or any combination of these.

11. The method of claim 1, wherein the calcium-bearing starting material is other than $CaCO_3$ or comprises a material other than $CaCO_3$.

12. The method of claim 1, further comprising regenerating a component of the aqueous solution.

13. The method of claim 1, wherein the first reacting step is performed at a temperature of at least 50 °C.

14. The method of claim 1, wherein the calcium salt is calcium chloride.

15. The method of claim 1, wherein the silicon compound comprises $SiO_2$.

16. The method of claim 1, wherein treating the calcium salt to produce a cement material comprises thermally treating the calcium salt in the presence of water to produce the cement material.

17. The method of claim 16, wherein thermally treating the calcium salt in the presence of water regenerates an acid.

18. The method of claim 17, wherein thermally treating the calcium salt to produce a cement material further comprises adding one or more additives to the calcium salt prior to treating.

19. The method of claim 18, wherein the one or more additives comprise a byproduct of the first reacting step and/or are formed from the one or more byproducts of the first reacting step.

20. The method of claim 18, wherein the one or more additives comprise a silicon compound.

21. The method of claim 1, further comprising treating the cement material to form a composite cement material.

22. The method of claim 21, wherein forming the composite cement material comprises thermally treating the cement material in combination with one or more additives.

23. The method of claim 22, wherein the one or more additives comprise a byproduct of the first reacting step and/or are formed from the one or more byproducts of the first reacting step.

24. The method of claim 22, wherein the one or more additives comprise an aluminum and/or iron compound.

25. The method of claim 22, wherein thermally treating is performed at a temperature of 1100 °C to 1800 °C.

26. The method of claim 21, wherein the composite cement material comprises Portland cement clinker.

27. The method of claim 1, further comprising producing one or more value- added side products.

28. The method of claim 27, wherein the value-added side products comprises a metal.

29. The method of claim 28, wherein the metal comprises Al, Mg, and/or Fe.

30. The method of claim 1, wherein the cement material is CaO.

* * * * *